(12) United States Patent
Denny

(10) Patent No.: US 9,501,623 B2
(45) Date of Patent: *Nov. 22, 2016

(54) PRESCRIPTION VERIFICATION SYSTEM

(75) Inventor: Lawrence A. Denny, Moore, OK (US)

(73) Assignee: NEVOCA.COM, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/572,851

(22) Filed: Aug. 13, 2012

(65) Prior Publication Data

US 2013/0173280 A1 Jul. 4, 2013

Related U.S. Application Data

(63) Continuation of application No. 12/845,232, filed on Jul. 28, 2010, now Pat. No. 8,244,587, which is a (Continued)

(51) Int. Cl.
G06G 1/14 (2006.01)
G06Q 20/00 (2012.01)
(Continued)

(52) U.S. Cl.
CPC ......... *G06F 19/3456* (2013.01); *G06Q 20/203* (2013.01); *G06Q 50/22* (2013.01); *G06Q 50/24* (2013.01)

(58) Field of Classification Search
CPC .................. G06Q 50/24; G06Q 10/087; G07F 17/0092; B65G 1/1373
(Continued)

(56) References Cited

U.S. PATENT DOCUMENTS 4,193,114 A 3/1980 Benini
4,695,954 A 9/1987 Rose et al.
(Continued)

FOREIGN PATENT DOCUMENTS

EP 937476 A2 * 8/1999

OTHER PUBLICATIONS

Robert Keet, "Essential Characteristics of an Electronic Prescription Writer", Journal of Healthcare Information Management, 1999. (Attached).*
(Continued)

*Primary Examiner* — Rokib Masud
(74) *Attorney, Agent, or Firm* — Dunlap Codding, P.C

(57) ABSTRACT

An apparatus for permitting a pharmacist to verify a refill of a filled prescription stored on a host system. A prescription refill screen is provided by the host system to a pharmacy system associated with the pharmacist. The prescription refill screen is associated with the filled prescription. Refill request information is received from the pharmacy system. The refill request information identifying a requested refill of the filled prescription. The refill request information is transmitted through the host system to a health care provider system associated with a health care provider identified by the filled prescription stored on the host system. The host system receives an authorization from the health care provider system authorizing the requested refill of the filled prescription. The host system transmits authorization to the pharmacy system whereby the pharmacist associated with the pharmacy system is authorized to provide the refill of the filled prescription to the patient.

13 Claims, 7 Drawing Sheets

Related U.S. Application Data continuation of application No. 11/724,467, filed on Mar. 15, 2007, now Pat. No. 7,801,765, which is a continuation of application No. 09/632,808, filed on Aug. 4, 2000, now abandoned, which is a continuation-in-part of application No. 09/400,498, filed on Sep. 21, 1999, now abandoned.

(51) Int. Cl.
    *G06F 19/00* (2011.01)
    *G06Q 20/20* (2012.01)
    *G06Q 50/22* (2012.01)
    *G06Q 50/24* (2012.01)

(58) Field of Classification Search
    USPC ............................................. 705/22, 26, 34
    See application file for complete search history.

(56) References Cited

U.S. PATENT DOCUMENTS

| | | | |
|---|---|---|---|
| 4,766,542 A | 8/1988 | Pilarczyk | |
| 4,847,764 A | 7/1989 | Halvorson | |
| 4,916,611 A | 4/1990 | Doyle, Jr. et al. | |
| 5,065,315 A | 11/1991 | Garcia | |
| 5,208,762 A | 5/1993 | Charhut et al. | |
| 5,737,539 A | 4/1998 | Edelson et al. | |
| 5,758,095 A | 5/1998 | Albaum et al. | |
| 5,845,255 A | 12/1998 | Mayaud | |
| 6,088,429 A * | 7/2000 | Garcia | G06F 19/322 379/67.1 |
| 6,202,923 B1 * | 3/2001 | Boyer | G06F 19/3462 235/375 |
| 6,493,427 B1 | 12/2002 | Kobylevsky et al. | |
| 6,687,676 B1 | 2/2004 | Denny | |
| 6,973,435 B1 | 12/2005 | Sioufi et al. | |
| 2005/0060200 A1 * | 3/2005 | Kobylevsky | G06F 19/3456 705/2 |

OTHER PUBLICATIONS

"Automated Identification of Relevant Patient Information in a Physician's Workstation"; by Henri J. Suermont, Ph.D., Paul C. Tang, M.D., Philip C. Strong, M.D., Charles Y. Young, Ph.D., and Jurgen Annevelink, Ph.D.; Hewlett Packard Laboratories, Palo Alto, California, Stanford University School of Medicine, Stanford, CA; 0195-4210/92/$5.00 © AMIA, Inc.

"Patient-Centered Computing: Can It Curb Malpractice Risk?", by Edward E. Bartlett, Ph.D., Department of Community and Family Medicine, Georgetown University School of Medicine; 0195/4210/92/$5.00 © AMIA, Inc.

"AskRX"; Drug Information Software for Microsoft Windows': Camdat Corporation, 359 Northgate Drive, Warrendale, PA, 15086. "Pharmacy Systems Review"; "Pharmacy Automation: Bitter Pills? or Spoonfuls of Sugar?"; healthcare informatics, Jun. 1993.

"necoma.com, Inc. Announces Development of World's Only On-Line Prescription Verification System"; PR Newswire; New York; Aug 16, 1999; p. 1-2.

* cited by examiner

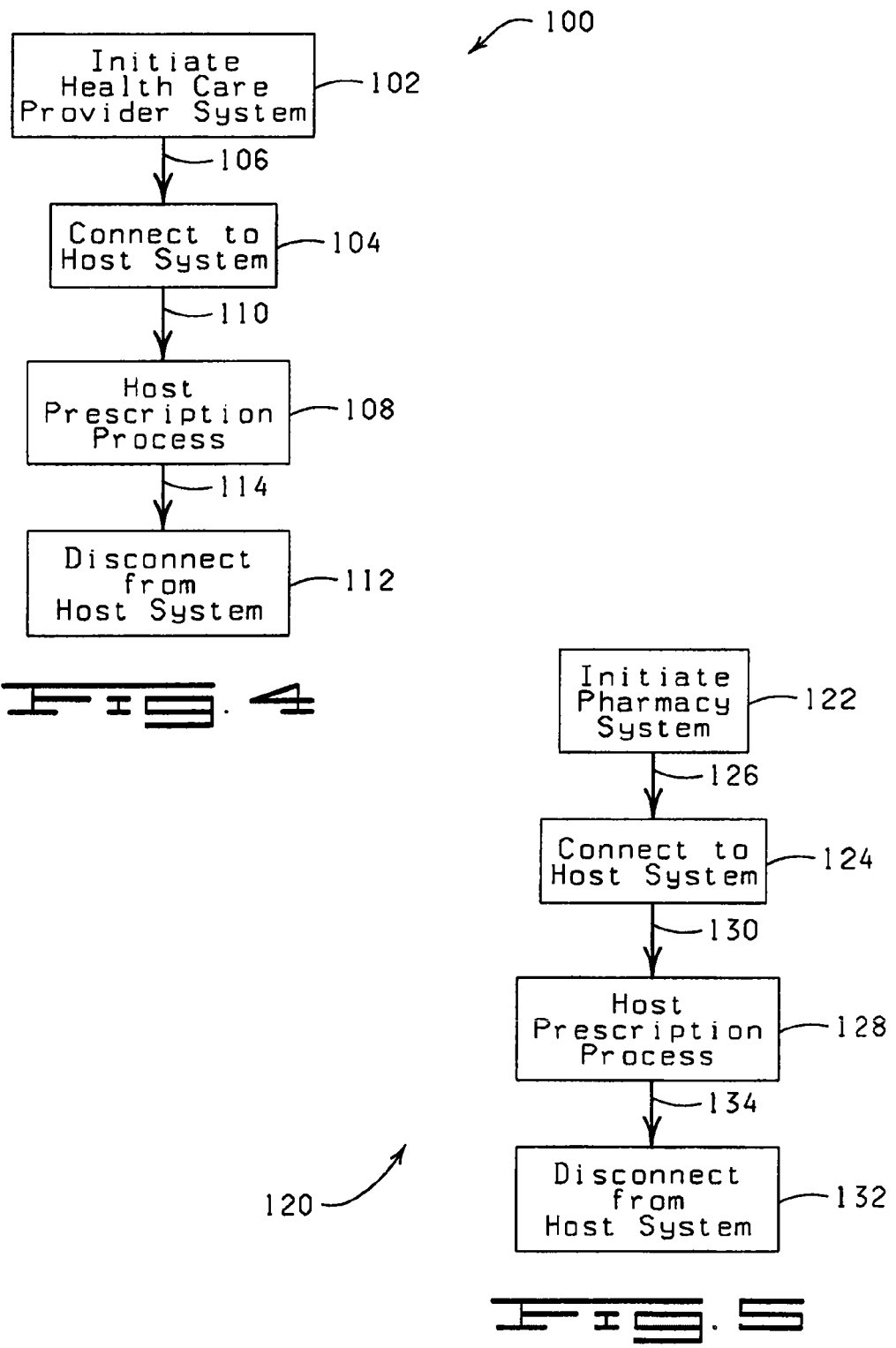

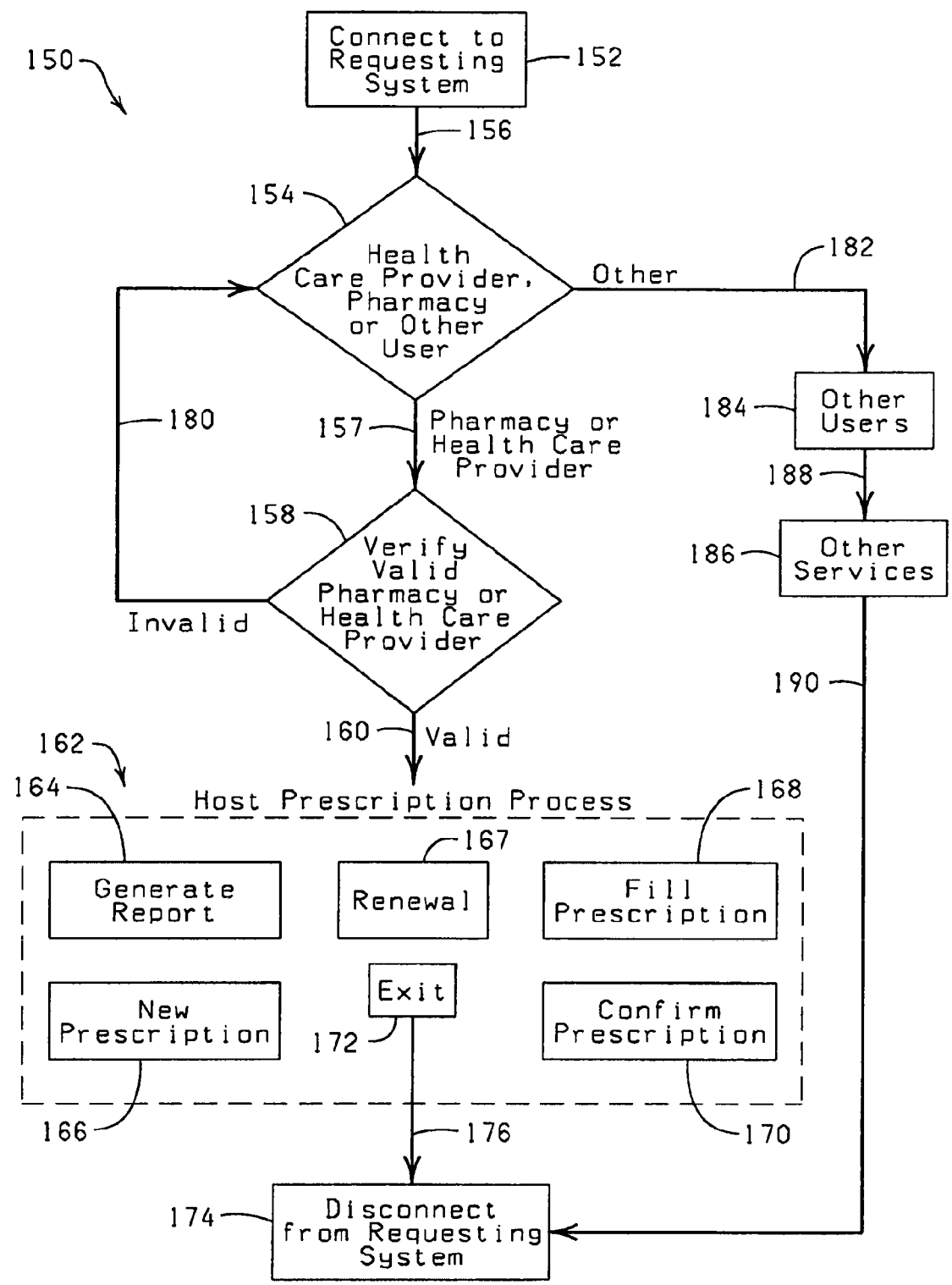

```
314                   302              316                  300
                       ↓                ↓                    ↓
   ┌─────────────────────────────────────────────────────┐
   │ Prescription#:12345-678-9101      Status: Filled    │
   ├─────────────────────────────────────────────────────┤
   │ Step 1: Patient Information                         │
   │                         First    Mid Int   Last     │
   │         Patient Name:   John     J         Doe      │
   │ Social Security Number: 1234-56-7891                │
304│         Date of Birth:  01/23/1972   MM/DD/YYYY     │
   │               Gender:   M                           │
   │      Medical Record #:  567                         │
   │   Consent form signed:  Yes      Consent Form       │
   │                                                     │
   │      This patient                 ┌────────┐        │
   │      has allergies.               │ Report │        │
   │         ☐                         └────────┘        │
   ├─────────────────────────────────────────────────────┤
   │ Step 2: Issuing Practitioner                        │
   │                         First              Last     │
306│     Practitioner Name:  Test               Doc      │
   │                DEA #:   999999                      │
   │      State License #:   987654                      │
   ├─────────────────────────────────────────────────────┤
   │ Step 3: Prescription Information                    │
   │             Medication: Acarbose                    │
   │               Strength: 250mg                       │
   │               Quantity: 30                          │
308│         Total Quantity: 150                         │
   │                    SIG: Take one tablet by mouth    │
   │                         once daily                  │
   │      Number of Refills: 4                           │
   │          Allow Generic: False                       │
   │  Prescription Confirmed: True                       │
   └─────────────────────────────────────────────────────┘
```

```
Step 4: Activity Status
    Total Quantity Filled:  150
        Refills to Date:  5
     Date of Last Refill:  11/10/99 10:48:58 AM PST
     Date of Last Partial:
```

312 →

```
Step 5: Request for Renewal
                    Date:─── 318              ─ 322
     Refill Qty. Authorized:╲          Qty. Filled:
        Authorization Code:╲ 320
         326 ─╱ Message 1:   ╲ 324
         328 ─╱ Message 2:
                                              ─ 332
         330 ─[ Send ]        [ Save ]
```

Fig. 8B

PRESCRIPTION VERIFICATION SYSTEM

CROSS-REFERENCE TO RELATED APPLICATIONS

This patent application is a continuation of U.S. Ser. No. 12/845,232, filed Jun. 28, 2010 (Now U.S. Pat. No. 8,244,587), which is a continuation of U.S. Ser. No. 11/724,467, filed Mar. 15, 2007 (Now U.S. Pat. No. 7,801,765), which is a continuation of U.S. Ser. No. 09/632,808, filed Aug. 4, 2000 now abandoned, which is a continuation-in-part of U.S. Ser. No. 09/400,498, filed Sep. 21, 1999 now abandoned, all three of which are hereby incorporated herein by reference.

BACKGROUND OF THE INVENTION

1. Field of the Invention

The present invention relates to a prescription verification system for maintaining information on pharmaceutical prescriptions, and more specifically, but not by way of limitation for verifying the validity and status of prescribed pharmaceuticals.

2. Prior Art

The prescription drug industry consists of several different organizations and professionals. These groups included the health care providers, pharmacies, insurance companies, federal agencies, state agencies, local agencies, and pharmaceutical firms. Each of these groups function virtually autonomous from the others, and each has its own specific interests. This autonomy, coupled with a lack of centralized information, frequently leads to errors in the ordering and filling of drug prescriptions, improper use of prescribed drugs, fraud within the system, and increased costs to each group within the industry.

There are approximately 630,000 prescribers of pharmaceuticals and 76,000 pharmacies in the United States which filled 2.6 billion prescriptions last year. It has been estimated that up to $25 billion per year is attributable to drug fraud and abuse. Additionally, the U.S. General Accounting Office suggests that inappropriate use of prescription drugs exceeds $20 billion per year. Although certain ones of the groups previously mentioned, namely the insurance companies, maintain information relating to their clients, there exists no nationally recognized or easily accessible system for maintaining information on prescription drugs to minimize fraud, abuse, and errors associated with the prescription drug industry.

Furthermore, prescriptions handwritten by physicians are frequently misinterpreted, or completely illegible to the filling pharmacist. Even where such handwritten prescriptions are partially legible, the patient is at great risk of the dosage and special instructions being incorrectly labeled on the final prescription.

Problems also exist with prescribed medications, since patients frequently are unaware of the specific type of medications they are currently taking or simply forget. This presents a serious problem since drug interactions may be dangerous, if not fatal. However, there does not exist a centralized system for a health care provider to determine current prescription medications that a specific patient may be using.

Thus, a need exists for a prescription verification system that is readily accessible to the groups previously mentioned, and more specifically, but not by way of limitation, to the health care provider which prescribes the medications and the pharmacies which fill the prescriptions. It is to a prescription verification system capable of minimizing the fraud, abuse and errors associated with prescription drugs that the present invention is directed.

SUMMARY OF THE INVENTION

The present invention relates to a prescription verification system for verifying prescriptions provided by a plurality of health care providers for a plurality of patients which can be filled through any one of a variety of patient-selected pharmacies. Each health care provider is provided with a health care provider system and each pharmacy is provided with a pharmacy system. In operation, a host system receives prescription information including a prescribed drug intended to treat a condition associated with a patient. The prescription information includes a dosage level for the prescribed drug, the drug label contents and any applicable notes to be included on the bottle, a unique health care provider code identifying the health care provider who input the prescription information, and a patient code uniquely identifying the patient.

In response to receiving the prescription information, a unique identification code associated with each prescription information is generated by the host system and the prescription information and the unique identification code associated with the prescription information are stored. Upon request, retrieval information based on the information associated with the prescription information received by the host system is transmitted to a patient-selected pharmacy system. The retrieval information includes the unique health care provider code identifying the health care provider who prescribed the prescription, the patient code uniquely identifying the patient, and the prescription information identifying the prescripted drug, dosage level, the drug label contents, and any applicable notes to be included on the bottle so that the pharmacist at the patient-selected pharmacy is provided with the necessary information to fill the prescription.

In another embodiment the present invention provides a prescription verification system for verifying pharmaceutical prescriptions provided by health care providers to patients which can be filled through any one of a variety of patient-selected pharmacies. The system includes a host system, a plurality of member health care provider systems, and a plurality of member pharmacy systems. The host system is capable of selectively receiving, storing and dispensing prescription information representative of a prescription for a patient and assigning a unique identification code associated with each prescription such that each prescription is selectively retrievable. The host system is also capable of receiving, storing, and dispensing information representative of the fulfillment of the prescription identified by the prescription information and assigning a confirmation code to the prescription information so as to indicate whether or not the prescription has been filled.

The plurality of member health care provider systems is remotely disposed from the host system and in communication with the host system. Each of the plurality of member health care provider systems is capable of receiving and inputting prescription information representative of the prescription for the patient into the host system, and is also capable of retrieving such prescription information. The plurality of member pharmacy systems is remotely disposed from the host system and in communication with the host system. Each of the plurality of member pharmacy systems is capable of inputting prescription information representative of the prescription for the patient into the host system and is also capable of receiving and inputting a confirmation code indicative of the prescription being filled into the host system upon fulfilling the prescription.

The present invention can further be provided with a refill option for authorizing and/or verifying a refill of a filled prescription stored on the host system. Thus, the refill becomes a part of the prescription history for the patient, which is available to the health care provider which prescribes the medications and the pharmacies which fill the prescriptions so as to reduce the effects of fraud and abuse on the health care system.

The advantages and features of the present invention will become apparent to those skilled in the art when the following description is read in conjunction with the attached drawings and the appended claims.

BRIEF DESCRIPTION OF THE DRAWINGS

FIG. 4. shows the elements and the logic flow diagram for a health care provider system.

FIG. 5. shows the elements and the logic flow diagram for a pharmacy system.

FIG. 6. shows the elements and the logic flow diagram for the host system of the prescription verification system.

FIGS. 8a and 8b show a computer entry screen for prescription refills of the prescription verification system depicted in FIG. 9.

DETAILED DESCRIPTION OF THE PREFERRED EMBODIMENTS

Figure 1:
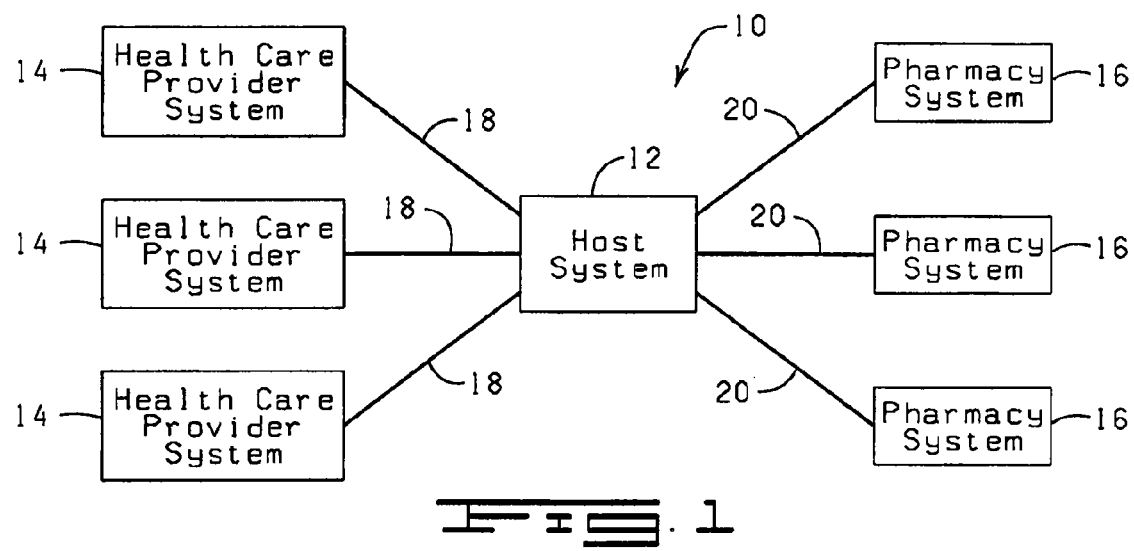
FIG. 1 is a diagram depicting a prescription verification system constructed in accordance with the present invention.

Referring now to the drawings and in particular to FIG. 1, shown therein is a prescription verification system 10 which is constructed in accordance with the present invention. The prescription verification system 10 includes a host system 12, a plurality of health care provider systems 14, and a plurality of pharmacy systems 16. The host system 12 can be any system, such as a computer system, which is capable of transmitting and receiving information from a large number of independent and/or non-affiliated systems, such as the health care provider systems 14 and the pharmacy systems 16 where the particular independent and/or non-affiliated systems, such as the health care provider systems 14 and the pharmacy systems 16, transmitting and/or receiving information from the host system 12 are not necessarily chosen by the owner of the host system 12. For example, the host system 12 can be an internet web site capable of transmitting and receiving information onto a public and/or global network, such as the world wide web.

The host system 12 is capable of selectively receiving, storing and dispensing prescription information representative of a prescription for a patient and assigning a unique identification code associated with each prescription such that each prescription is selectively retrievable by the unique identification code, or other information associated with the prescriptions. The host system 12 is also capable of receiving, storing, and dispensing information representative of the fulfillment of the prescription identified by the prescription information and assigning a confirmation code to the prescription information so as to indicate whether or not the prescription has been filled.

The plurality of health care provider systems 14 may be any computer system capable of communicating with the host system 12, such as a personal computer with a web browser, Web TV, or a personal digital assistant. The plurality of health care provider systems 14 are shown in communication with the host system 12 via a communication channel 18. The communication channel 18 may be any communication median capable of transmitting information between the health care provider system 14 and the host system 12, such as an analog or digital telephone line, fiber-optic line, wireless or other electronic communication median for communication between the host system 12, the health care provider system 14 and the pharmacy system 16.

It should be noted that the communication industry is rapidly advancing and there is sure to be communication media developed in the future. It is envisioned that the present invention will also utilize the newly developed communication medians.

The plurality of member health care provider systems 14 are remotely disposed from the host system 12 and in communication with the host system 12. Each of the plurality of member health care provider systems 14 is capable of receiving and inputting prescription information representative of the prescription for the patient into the host system 12, and is also capable of retrieving such prescription information.

The plurality of pharmacy systems 16 may be any computer system capable of communicating with the host system 12, such as a personal computer with a Web browser, Web TV, or a personal digital assistant. The plurality of pharmacy systems 16 are shown in communication with the host system 12 via a communication channel 20. The communication channel 20 may be any communication median capable of transmitting information between the pharmacy system 16 and the host system 12, such as an analog or digital telephone line, fiber-optic line, wireless or other electronic communication median as discussed above with reference to the communication channel 18.

The plurality of member pharmacy systems 16 are remotely disposed from the host system 12 and in communication with the host system 12. Each of the plurality of member pharmacy systems 16 is capable of inputting prescription information representative of the prescription for the patient into the host system 12 and is also capable of receiving and inputting a confirmation code indicative of the prescription being filled into the host system 12 upon fulfilling the prescription.

The prescription verification system 10 is capable of verifying prescriptions provided by the plurality of health care providers, such as physicians, physicians assistants, and administrative individuals associated with the health care provider, for a plurality of patients which can be filled through any one of the variety of patient-selected pharmacies. The health care providers may be affiliated or not affiliated with other health care providers, such as hospitals and hospital affiliated physicians, or unaffiliated clinics and physicians, or combinations thereof. Also, the patient-selected pharmacies may be affiliated or not affiliated with each other, such as Eckerd Drug, Wal-Mart, and\or other independent pharmacies. In other words, each health care provider, such as a doctor, is provided with the health care provider system 14 and each pharmacy is provided with the pharmacy system 16.

In operation, the host system 12 receives prescription information via the communication channel 18 from the health care provider system 14. The prescription information includes a prescribed drug intended to treat a condition associated with a patient. The prescription information also includes a dosage level for the prescribed drug, the drug label contents and any applicable notes to be included on the bottle given to the patient and containing the prescribed drug, a unique health care provider code identifying the health care provider who prescribed the drug, and a patient code uniquely identifying the patient. It should be understood that the term "bottle" as used herein refers to any type of container capable of containing the prescribed drug. The prescription information may also include similar information regarding previous prescriptions which have been prescribed by the health care provider to the patient and whether or not the previous prescriptions have been filled by the pharmacist.

In response thereto, the host system 12 generates a unique identification code associated with each prescription information, and the prescription information is stored by the host system 12, including the unique identification code associated with the prescription information. Upon request, the host system 12 transmits retrieval information based on the information associated with the prescription information received by the host system 12 to a patient-selected pharmacy system 16 via communication channel 20. The retrieval information including the unique health care provider code identifying the health care provider, the patient code uniquely identifying the patient, and the prescription information identifying the prescripted drug and dosage level. Thus it can be seen that the prescription verification system 10 allows pharmacists to verify pharmaceutical prescriptions provided by health care providers to patients which can be filled through any one of a variety of patient-selected pharmacies.

Figure 2:
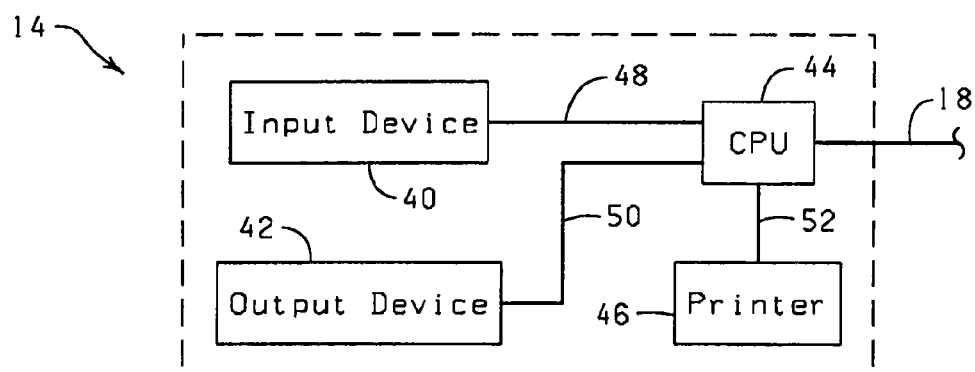
FIG. 2 is a schematic, diagrammatic representation, in more detail, of one embodiment of the health care provider system depicted in FIG. 1.

Referring now to FIG. 2, one embodiment of the health care provider system 14 is shown. The health care provider system 14 includes an input device 40, an output device 42, a central processing unit (CPU) 44, a printer 46, and the communication channel 18. The users of the health care provider system 14, such as physicians, physicians assistants, nurses, and administrative personnel associated with the health care provider, input information representative of a prescription for a patient into the health care provider system 14 via the input device 40. The input device 40 can be any device capable of inputting information into the health care provider system 14, such as a keyboard, mouse, scanner, voice-recognition, or other similar devices. The information input into the input device 40 is transmitted along line 48 to the central processing unit 44 for communication to the host system 12 (see FIG. 1) via the communication channel 18.

The health care provider system 14 is capable of receiving prescription information from the host system 12 (see FIG. 1), pursuant to a request from the health care provider system 14, via the communication channel 18. The prescription information received from the host system 12 is processed by the central processing unit 44 and transmitted to the output device 42, via line 50, or the printer 46 via line 52, where the prescription information is capable of being perceived by the user of the health care provider system 14. The output device 42 can be any device capable of outputting information in a format perceivable by an individual, such as a computer monitor. The printer 46 may be any means of outputting prescription information, such as prescription forms printed by a laser printer.

Figure 3:
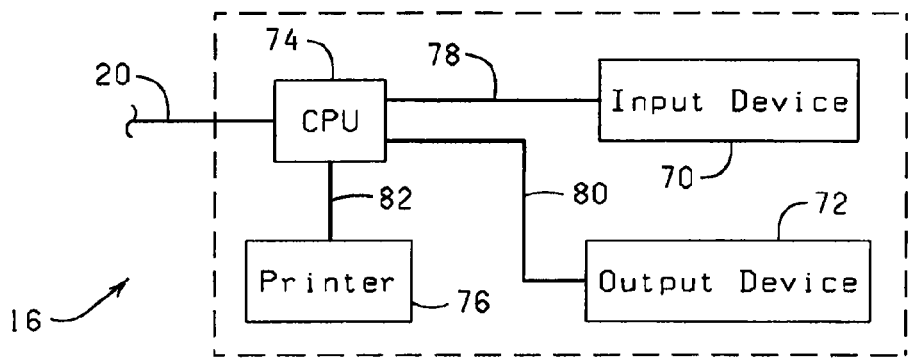
FIG. 3 is a schematic, diagrammatic representation, in more detail, of one embodiment of the pharmacy system depicted in FIG. 1.

Referring now to FIG. 3, one embodiment of the pharmacy system 16 is shown. The pharmacy system 16 includes an input device 70, an output device 72, a central processing unit (CPU) 74, a printer 76, and the communication channel 20. The users of the pharmacy system 16, such as pharmacists, pharmacists assistants, and administrative personnel associated with the pharmacy, can input information representative or indicative of a prescription to be filled into the pharmacy system 16 via the input device 70 to retrieve the retrieval information discussed above, and, in some instances when authorization is obtained by a physician, to input the prescription information. The input device 70 may be any device capable of inputting information into the pharmacy system 16, such as a keyboard, mouse, scanner, voice-recognition, or other similar devices. The information input into the input device 70 is transmitted along line 78 to the central processing unit 74 for communication to the host system 12 via the communication channel 20.

The pharmacy system 16 is capable of receiving retrieval information, such as information indicative of a prescribed drug intended to treat a condition associated with a patient, and a dosage level for the prescribed drug, the drug label contents and any applicable notes on the bottle, a unique health care provider code identifying the health care provider, and a patient code uniquely identifying the patient from the host system 12, via the communication channel 20. The retrieval information is processed by the central processing unit 74 and transmitted to the output device 72, via line 80, or the printer 76 via line 82, where the retrieval information is capable of being perceived by the user of the pharmacy system 16. The output device 72 can be any device for outputting information in a format perceivable by and individual, such as a computer monitor. The printer 76 can be any means of outputting the retrieval information, such as prescription labels printed by a laser printer.

The pharmacy system 16 is also capable of inputting a confirmation code indicative of the prescription being filled into the host system 12. The confirmation code is input by the user of the pharmacy system 16 into the input device 70 and transmitted to the host system 12 via the central processing unit 74, and via line 78 and communication channel 20 so that the confirmation code is available to any health care provider system 14 or pharmacy system 16 which retrieves the information associated with the prescription. In this way, the problems associated with the repetitive filling of prescriptions is eliminated.

Referring now to FIG. 4, a logic flow diagram of a connection sequence 100 for the health care provider system 14 (see FIG. 1) is shown. The first step 102 is to initiate the health care provider system 14 which may be accomplished, for example where the health care provider system 14 is a personal computer, by powering on the personal computer and launching Internet browsing software, such as Microsoft Internet Explorer. Then, the health care provider system 14 connects to the host system 12 (see FIG. 1) using communication methods well-known in the art or developed in the future as indicated in FIG. 4 by a step 104 and a line 106.

Once the health care provider system 14 connects to the host system 12, the host system 12 processes prescription information received from the health care provider system 14 as indicated in FIG. 4 by a step 108 and a line 110. During the step 108, new prescription information may be input into the host system 12 by the health care provider system 14, and information regarding previously entered prescriptions for the patient prescribed by any health care provider, which are stored in the host system 12, such as previously prescribed and/or filled prescriptions (hereinafter referred to as the patient's "prescription history"), can be received by the health care provider system 14 from the host system 12. This permits the health care provider to take appropriate action based upon the patient's prescription history, or cancel any unfilled prescriptions. After a new prescription has been entered into the host system 12, a printout of the prescription information including the unique code generated by the host system 12 is provided by the printer 46 (FIG. 2) and the printout is presented to the patient, if desired. Thereafter, the health care provider system 14 disconnects from the hosts system 12, such as by terminating the Internet browsing software of the health care provider system 14 as indicated in FIG. 4 by a step 112 and a line 114.

Referring now to FIG. 5, a logic flow diagram of a connection sequence 120 for the pharmacy system 16 (see FIG. 1) is shown. The first step 122 is to initiate the pharmacy system 16 which may be accomplished, for example where the pharmacy system 16 is a personal computer, by powering on the personal computer and launching an Internet browsing software, such as Microsoft Internet Explorer. Thereafter, the pharmacy system 16 connects to the host system 12 (see FIG. 1) using communication methods as discussed above, as indicated in FIG. 4 by a step 124 and a line 126.

Once the pharmacy system 16 is connected to the host system 12, the host system 12 processes prescription information received from the pharmacy system 16 during a step 128 and a line 130. For example, after receiving a prescription, the patient can travel to one of the patient-selected pharmacies and present the printout of the prescription information to a pharmacist. The pharmacist enters the unique code identifying the prescription or other information identifying the patient into the pharmacy system 16 to effect retrieval of the prescription from the host system 12. During the step 128, the patient prescription information is received by the pharmacy system 16 from the host system 12, the prescription is filled by the pharmacist associated with the pharmacy system 16, and a confirmation codes indicative of a prescription being filled is input into the host system 12 by the pharmacy system 16. Thereafter, the pharmacy system 16 disconnects from the host system 12, such as by terminating the Internet browsing software of the pharmacy system 16 as indicated in FIG. 4 by a step 132 and a line 134.

Referring now to FIG. 6, a logic flow diagram 150 for the host system 12 (see FIG. 1) of the prescription verification system 10 is shown. Once the health care provider system 14 or the pharmacy system 16 has initiated the connection sequence 100 and 120, respectively, to connect to the host system 12, the host system 12 proceeds to a first step 152 where the host system 12 connects to such requesting health care provider system 14, pharmacy system 16, or other user, such as an insurance company, federal government organization, or other user. The host system 12 can maintain an introductory or welcome home page screen accessible to all users, such as internet users. Such screen or screens desirably provide information regarding the prescription verification system 10, administrative and advertising information, hypertext links to related Internet web sites and other information beneficial to the use and promotion of the prescription verification system 10. Then, the software running on the host system 12 proceeds to a step 154 along a line 156 to determine the identity of the requesting system.

When the requesting system requests access to the health care provider system 14 or the pharmacy system 16 services on the host system 12, the process branches to a step 158 as indicated by line 157 to verify that the requesting system is a valid health care provider system 14 or pharmacy system 16. The verification screen determines that the requesting system is a valid health care provider system 14 or pharmacy system 16, by using password protection or other security methods known in the art.

The determination that the requesting system is a valid health care provider system 14 or pharmacy system 16 causes the process to branch to a host prescription process 162 as indicated by a line 160. The host prescription process 162 provides the health care provider system 14 or pharmacy system 16 a variety of options, including a generate report option 164, a new prescription option 166, a refill option 167, a fill prescription option 168, a confirm prescription option 170, and an exit option 172 to exit the host system 12. Once the valid health care provider system 14 or pharmacy system 16 completes the host prescription process 162 the next step 174, along a line 176, is for the host system 12 to disconnect from the health care provider system 14 or the pharmacy system 16.

The determination at the verification step 158 that the requesting system is not a valid health care provider system 14 or pharmacy system 16 causes the process to return to step 154 which allows the requesting system to re-select host system 12 services as indicated by a line 180.

Where the requesting system at the step 154 requests other services, such as general information regarding the prescription verification system 10 as previously discussed, the process branches to a step 184 as indicated by a line 182. The other user may select from a variety of other services offered by the host system 12 which causes the process to advance to the next step 186, along a line 188, which provides access to other host system 12 services. The services may include access to non-sensitive prescription information that are of interest to organizations such as insurance companies, federal organizations such as the Drug Enforcement Administration and Medicare, and other organizations desirous of obtaining information regarding pharmaceutical prescriptions maintained in a secure and centralized system.

Additionally these other services may include, as previously discussed, applications and information for becoming a member of the prescription verification system 10 and thus a valid health care provider system 14 or pharmacy system 16, and a discussion of the costs and obligations of such membership. Hyper-links to other organizations of interest as well as general health care related information will be available at the step 186. It will be appreciated that the step 186, as those above, may include a plurality of Internet web pages capable of communicating and receiving the information between the other users and the host system 12. Once the other user completes the other services step 186 the program branches to the step 174, along a line 190, to disconnect from the requesting system.

Figure 7:
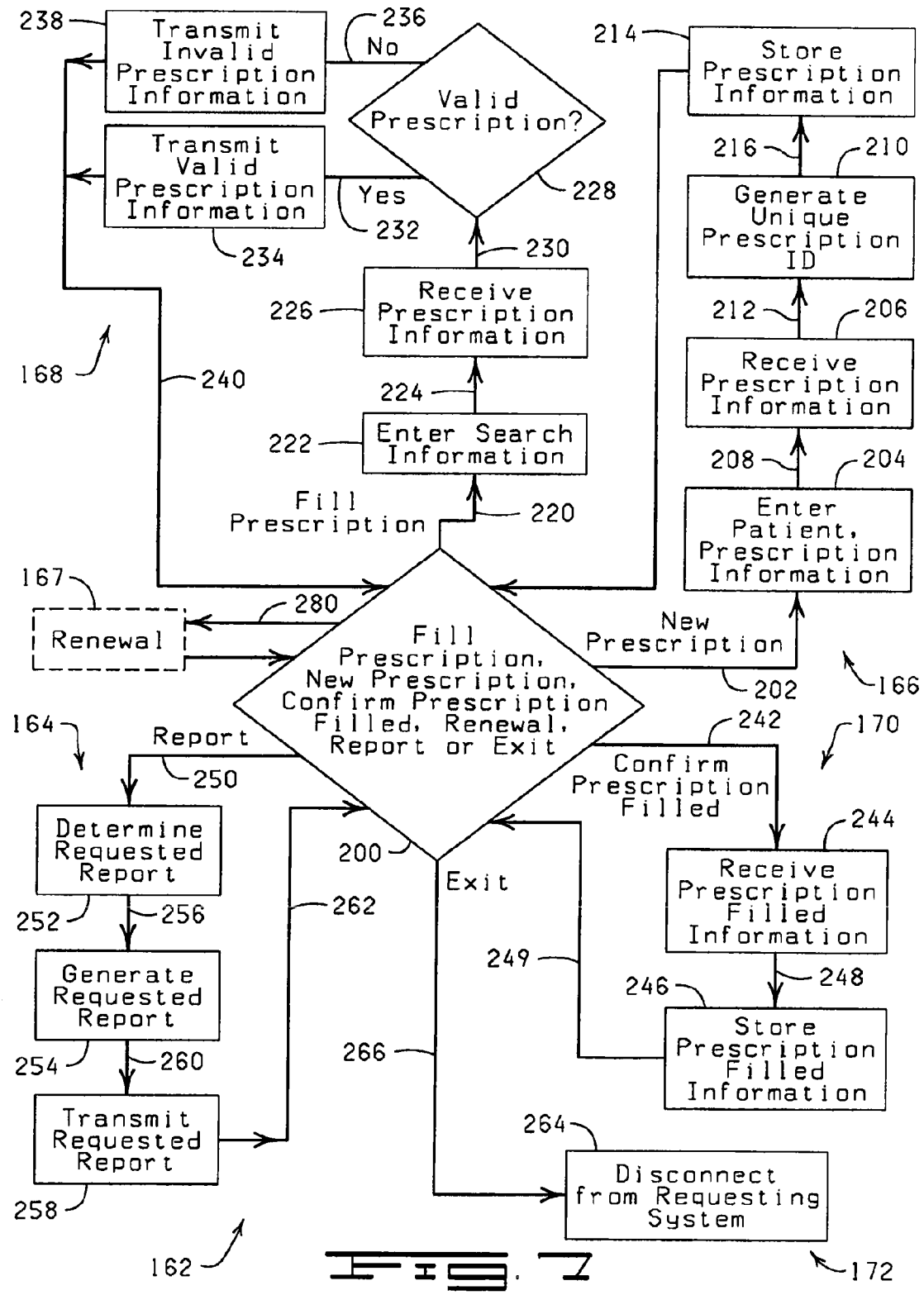
FIG. 7. shows the elements and the logic flow diagram, in more detail, of one embodiment of the host prescription process depicted in FIG. 6.

Referring now to FIG. 7, the host prescription process 162 is shown in more detail. The host prescription process 162 presents the health care provider system 14 (see FIG. 1) and the pharmacy system 16 with a step 200 for selecting a variety of options which may include generate report option 164, new prescription option 166, refill option 167, fill prescription option 168, confirm prescription option 170, and exit option 172 for exiting the host system 12.

In response to the health care provider system 14 or the pharmacy system 16 selecting the new prescription option 166, the process branches to the step 204, as indicated by a line 202, wherein prescription information is entered into the host system 12. Prescription information includes, but is not limited to, patient information such as name, address, telephone and social security number, the prescribed drug, the patient's condition intended to be treated, a dosage level for the prescribed drug, the drug label contents, and any applicable notes which are intended to appear on the label of the bottle, an identifying code uniquely associated with the health care provider, and a patient code uniquely associated with the patient.

It should be appreciated that frequently patients require prescription drugs after normal health care provider hours which are telephoned into a patient-selected pharmacy by the health care provider. In such an event, the prescription verification system 10 allows the pharmacy system 16 in this step 204 to enter the prescription information along with the information about the health care provider which telephoned the prescription to the pharmacy. The inputting of the identifying code uniquely associated with the health care provider is a security measure against fraudulently telephoned prescriptions, while remaining flexible to the realities of modern health care.

At a step 206, along a line 208, the host system 12 receives the prescription information which was previously entered. It will be understood that certain steps, such as data validation, have been omitted since such steps are well known in the art. Thereafter, the process branches along a line 210 to a step 212, where the host system 12 generates a unique prescription identification number. This unique prescription number is associated in the database with the corresponding prescription information. Once the unique prescription identification number is generated, the process branches to a step 214, along a line 216, where the host system 12 stores the prescription information and the unique prescription identification number associated therewith in a database accessible by the host system 12. The process then returns along a line 218 to the options step 200.

Where it is determined that the health care provider system 14 or pharmacy system 16 has selected fill prescription 168, the process branches to a step 222 along a line 220 where search information is entered. The search information which may be used to search the prescription verification system 10 database may include, but is not limited to, the unique prescription identification number, the patient's social security number or name, and the health care provider name or unique code associated therewith. The search information may also include a pharmacy code or a license number associated with the pharmacist filling the prescription, a pharmacy prescription code and unique code associated with the pharmacy system 16. The search information is received by the host system 12 at a step 226, as indicated by a line 224. It should be noted that when the database wherein the prescription information is maintained includes a confirmation code field, i.e. the confirmation code, intended to identify whether or not a prescription has been filled, the confirmation code is communicated with the prescription information.

Thereafter, the host system 12 determines whether or not the data received is valid based upon querying the prescription database by a step 228, as indicated by a line 230. Where the information received from the pharmacy system 16 corresponds to prescription information maintained in the host system 12 database, the process branches to a step 234, indicated by a line 232, and transmits a signal to the health care provider 14 or pharmacy system 16 indicating that the prescription information entered is valid. However, where the information received from the pharmacy system 16 does not correspond to prescription information maintained in the host system 12 database, the process branches to a step 238, as indicated by a line 236, and transmits a signal to the health care provider system 14 or pharmacy system 16 indicating that the prescription information entered is invalid.

As a further security measure, upon receiving the prescription information by the pharmacy system 12, the pharmacist may determine, based upon the value of the confirmation code field in the prescription information, that the prescription has been previously filled and therefore may not now be filled. The process then proceeds along a line 240 to the options step 200.

Where it is determined that the health care provider system 14 or the pharmacy system 16 has selected confirm prescription 170, the process branches 242 to the step 244 of receiving prescription filled information. As previously discussed, the prescription information includes a confirmation code which can be an identifier field associated with each prescription indicating whether the prescription has been filled. When a pharmacy system 16 transmits prescription information indicative of a prescription having been filled, the host system 12 modifies the confirmation code so as to indicate that the prescription has been filled. The next step 246, along a line 248, is for the host system 12 to store the prescription information including the confirmation code so as to indicate that the prescription has been filled. Thereafter the process returns to the options step 200, as indicated by a line 249.

Where it is determined that the health care provider system 14 or the pharmacy system 16 has selected generate reports 164, the process branches to a step 252, as indicated by a line 250, to determine the requested report. During this step 252, the health care provider system 14 and pharmacy system 16 are presented with a selection of reports which may be generated by the host system 12 based upon prescription information data maintained in the prescription database by the host system 12. These reports may include prescription data summarized by patient name, social security number, the name of the prescribing health care provider, the physician's Drug Enforcement Agency (DEA) number, and time and transaction based reporting such as daily, monthly prescription reports, and other useful means of organizing and presenting prescription information.

Once the type of report has been selected by the health care provider system 14 or pharmacy system 16 the process branches to a step 254, along a line 256, for the host system 12 to generate the report from the prescription information database. Thereafter the host system 12 transmits, as indicated by a step 258, along a line 260, the requested report from the host system 12 to the requesting health care provider system 14 or pharmacy system 16. Thereafter, the process returns to the options step 200, as indicated by a line 262.

Where the health care provider system 14 or the pharmacy system 16 selects to exit the host system 12 from the option step 200, the system branches to the step 264, as indicated by a line 266, and disconnects from the health care provider system 14 or pharmacy system 16. It will be appreciated that the prescription verification system 10 may include other procedures and utilities, such as software routines located on the host system 12 for maintaining and utilizing an Internet web site and commonly utilized by similarly situated Internet web site systems. Such utilities and routines are well known in the art and a detailed description is deemed unnecessary herein to teach one skilled in the art to practice the present invention.

It should be appreciated that patients require refills of prescription drugs after the patient has completely filled the prescription. To validate a refill of prescription drugs, the health care provider at one of the health care provider systems 14 or a pharmacist at one of the pharmacy systems 16 selects the refill option 167 shown in FIG. 6.

Referring now to FIG. 8, an entry screen 300 constructed in accordance with the present invention is shown. The entry screen 300 is an example of a data entry screen as presented on the health care provider system 14, or the pharmacy system 16 for displaying information associated with a prescription.

The entry screen 300 includes a heading section 302, a patient information section 304, a practitioner information section 306, a prescription information section 308, an activity status section 310, and a prescription refill section or screen 312.

The heading section 302 preferably includes a prescription number field 314 having stored therein the unique prescription identification number uniquely associated with the prescription. The heading section 302 is provided with a status field 316, which indicates whether or not the prescription has been filled. In the example shown in FIG. 8, the prescription identified by the unique prescription identification number "11543-981-004" is indicated to be "filled".

The patient information section 304 includes various information to identify the patient, such as the patient name, patient's social security number, patient's date of birth, gender or the like. In addition, an allergy alert message 304a and a click button 304b are also provided in the patient information section 304. If it has been indicated that the patient has allergies, the allergy alert message 304a will appear on the patient information section 304, to alert the member, i.e. the health-care provider or the pharmacist, of the allergy. The member can click on the click button 304b to open a table that lists the allergies, if desired. If authorized, the member can edit the table to provide a new allergy.

Furthermore, it should be noted that consent forms are required at both the health-care provider side and the pharmacy side of the system 10. A patient consent form is available for printing from the system 10, as indicated by a consent message 305a. Once a consent form has been signed, a consent form indicator 305b is provided on the patient information section 304 to indicate that the consent form has been signed. Although the consent form indicator 305b has been shown and indicated as the term "yes", to indicate that the consent form has been signed, it should be understood that the signed consent form indicator 305b could take other forms.

In addition, it should be noted that the consent forms are only valid for a predetermined time, such as six months. Once the predetermined time has expired, the consent form indicator 305b will change to indicate that a new consent form needs to be signed before further medications or prescriptions are dispensed. For example, the consent form indicator 305b can change to the term "no", to indicate that a new consent form needs to be signed.

The practitioner information 306 contains information to uniquely identify the particular health care provider which prescribed the prescription identified in the prescription number field 314. For example, the practitioner information section 306 may include the name of the health care provider, the DEA number of the health care provider, or the state license number of the health care provider, and combinations thereof.

The prescription information section 308 includes various information associated with the prescription prescribed by the health care provider identified in the practitioner information section. For example, the prescription information section 308 may include information on the type of medication, the strength of the medication, a partial refill quantity, a total quantity, suggested notes to be included on the bottle, the number of refills, whether or not to allow generic medications, and whether the prescription has been confirmed.

The activity status section 310 contains a variety of information with respect to the status of the prescription, such as a total quantity filled which maintains information relevant to the cumulative number of medication units which have been dispensed to date, refills to date which indicates the cumulative number of refills for the prescription, a last refill date and a last partial refill date.

When the status field 316 in the heading section 302 indicates that the prescription has not been entirely filled, only the information section 304, the practitioner information section 306, the prescription information section 308 and the activity status section 310 are displayed and quantities of the medication can be filled up to the total amount indicated in the total quantity field of the activity status section 310. However, where the status field 316 of the heading section 302 indicates that the prescription has been entirely filled, only then will the prescription refill section 312 be visible to the pharmacist or health care providers utilizing the pharmacy system 16 or the health care provider systems 14.

The prescription refill section 312 preferably includes a date field 318, a refill quantity authorized field 320, a quantity filled field 322, an authorization code field 324, a first message field 326, and a second message field 328. The fields 318, 320, 322, 324, 326 and 328 will be described in more detail below.

The entry screen 300 is preferably provided with a send button 330 and a save button 332 for purposes to be described hereinafter.

Figure 9:
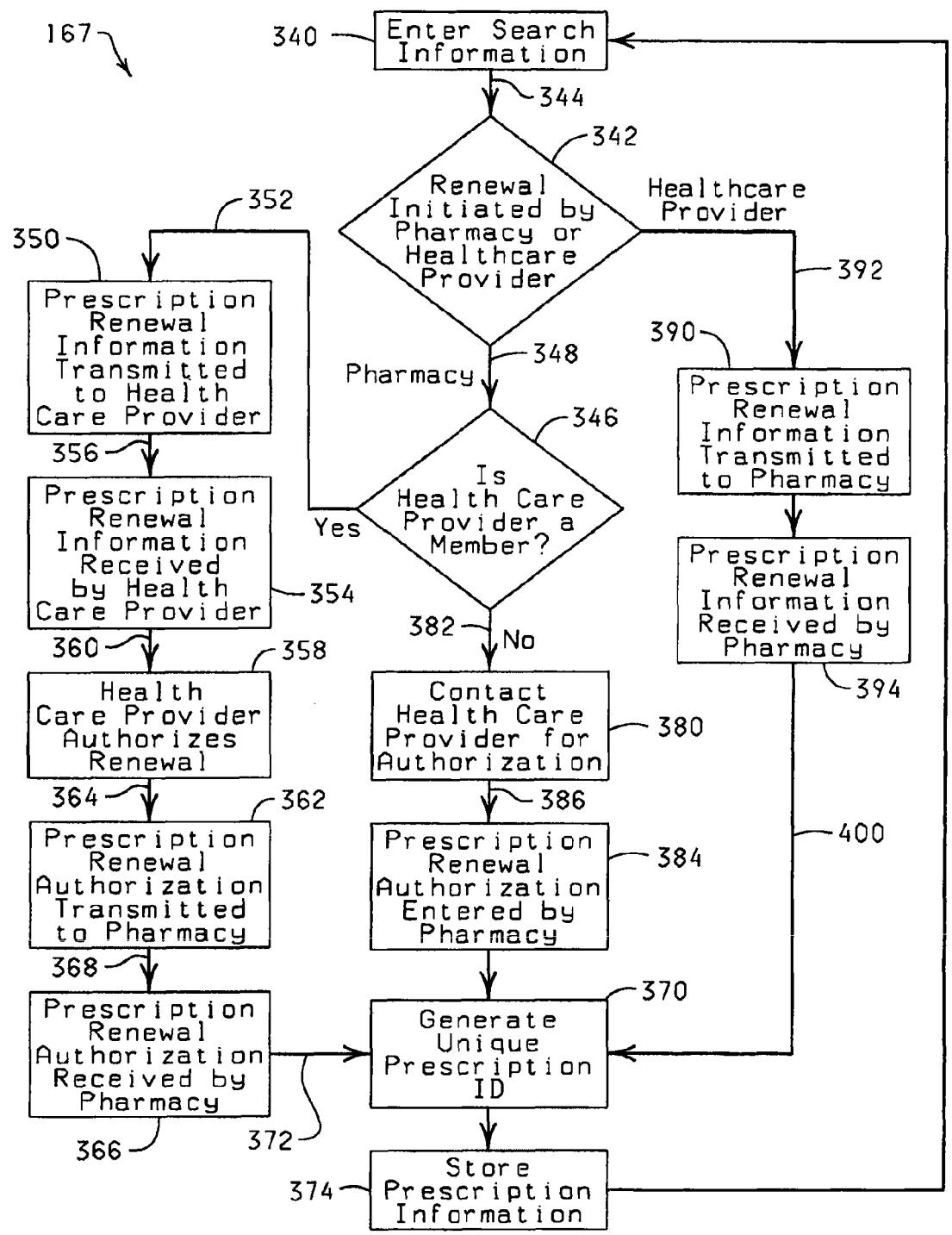
FIG. 9 shows the elements and the logic flow diagram, in more detail, of a refill option of the host prescription process depicted in FIGS. 6 and 7.

Referring now to FIG. 9 in combination with FIG. 8, shown therein is a logic flow diagram of the refill option 167. Once the process branches to the refill option 167, refill request information and an authorization are received by the host system 12 for producing a "new" prescription based on a filled prescription stored on the host system 12. As will be discussed in more detail below, the refill request information, and the authorization can be entered in by either the health care provider at the health care provider system 14, a pharmacist at one of the pharmacy system 16 or combinations thereof.

Once the refill option 167 has been initiated, search information is entered into the host system 12 so as to locate the particular filled prescription in the data base to be refilled, as indicated by a block 340. The search information can be the unique prescription identification number contained in the prescription number field 314, or any of the various information in the patient information section 304, such as the patient's name or social security number, for example.

Once the search information is entered into the host system 12, the host system 12 retrieves all of the information in the host system 12 regarding the filled prescription of the patient.

The host system 12 then branches to a step 342 as indicated by a line 344. In the step 342, the host system 12 determines whether or not the refill option 167 was initiated by a health care provider system 14 or a pharmacy system 16. If the host system 12 determines that the refill option 167 was initiated by a pharmacy system 16, the host system 12 branches to a step 346 as indicated by a line 348. The host system 12 then determines whether the health care provider which is indicated in the practitioner information section 306 as issuing the filled prescription is a member of the prescription verification system 10. If the health care provider is a member of the prescription verification system 10, the host system 12 branches to a step 350 as indicated by a line 352.

In the step 350, the host system 12 receives refill request information from the pharmacy system 16. The refill request information identifies a requested refill of the filled prescription. The refill request information may include the current date filled into the date field 318, and any desired message from the pharmacist to the health care provider in the first message field 326 (see FIG. 8). The refill request information is then transmitted through the host system 12 to one of the health care provider systems 14 associated with the health care provider identified by the practitioner information section 306 of the filled prescription stored on the host system 12. In one preferred embodiment, the refill request information is transmitted through the host system 12 to the health care provider system 14 so as to maintain the information contained in the refill request information secure.

The refill option 167 then branches to a step 354 as indicated by a line 356 where the refill request information is received by the health care provider system 14 associated with the health care provider designated for verification purposes. For example, in one preferred embodiment, the refill request information is immediately delivered to a message box associated with the host system 12 for delivery to the health care provider designated for verification purposes. If the health care provider system 14 happens to be logged onto the prescription verification system, an indicator is immediately output by the health care provider system 14 to notify the health care provider that the refill request information has arrived. If the health care provider system 14 is not logged onto the prescription verification system, then during log in of the health care provider system 14 to the host system 12, an indicator is displayed or otherwise output to the health care provider that a message has been received in their message box.

The health care provider reads the refill request information and then authorizes the refill at a step 358 (as indicated by a line 360) if the health care provider identifies the prescription refill information as a valid refill of a drug prescription to be refilled for a patient of the health care provider. If the health care provider does not authorize the refill, then the refill option 167 ends. In one preferred embodiment, the health care provider provides authorization by filling in the refill quantity authorized field 320 of the prescription refill section 312.

The authorization may also include a message placed into the second message field 328, if desired, by the health care provider. The health care provider then transmits the authorization to the host system 12 in a step 362, as indicated by a line 364. The host system 12 immediately delivers the authorization to the pharmacy system 16 which initiated the refill request information. The authorization is then received by the pharmacy system 16, and a notification is provided to the pharmacist that the authorization has been received at a step 366 as indicated by a line 368. For example, the pharmacist may receive an audio or video message on the pharmacy system 16 indicating that there is a message from a member of the prescription verification system 10 which requires a response. The pharmacist then reads the information contained in the authorization and enters the quantity of the medication filled into the quantity filled field 322 of the prescription refill section 312 and then clicks on the save button 332 to indicate that the refill request has been completed.

The refill option 167 then branches to a step 370, as indicated by a line 372, where the host system 12 generates a new, unique prescription identification number uniquely identifying the refill of the filled prescription. In one embodiment, the new unique prescription identification number of the refill consists of the unique prescription identification number of the filled prescription with a "R" suffix added. The refill prescription is now considered by the host system 12 as a "new" prescription in the data base and partial fills etc. would be handled like any new prescription.

It should be noted that once the new unique prescription identification number is generated, the data base record of the new unique prescription identification is auto populated with the appropriate information from the record identifying the filled prescription upon which the refill prescription was based as indicated by a block 374.

If the host system 12 determines at the step 346 that the health care provider designated for verification purposes is not a member of the prescription verification system 10, the refill option 167 branches to a step 380, as indicated by a line 382. At the step 380, the pharmacist contacts the health care provider via telephone, facsimile, e-mail or the like, to obtain the health care provider's authorization via devices and/or method external to the host system 12. Assuming that the health care provider provides authorization for the refill, the refill option 167 branches to a step 384, as indicated by a line 386 where the pharmacist enters in refill request information identifying a requested refill of the filled prescription and a prescription refill authorization obtained from the health care provider. For example, the pharmacist may enter the current date into the date field 318, an authorization approval into the authorization code field 324, a quantity into the refill quantity authorized fields 320 or quantity filled field 322, and any desired message into either one or both of the first and second message fields 326 and 328. The pharmacist then utilizes the pharmacy system 16 to click on the save button 332 whereby the refill request information is transmitted from the pharmacy system 16 to the host system 12 and thereafter received and stored by the host system 12.

The refill option 167 then branches to the step 370 as indicated by a line 386. The step 370 was described hereinbefore with reference to FIG. 9 and will not be redescribed herein for purposes of clarity.

If at the step 342, it is determined that a health care provider system initiated the refill option 167, the process branches to a step 390, as indicated by a line 392. At the step 390, the prescription refill screen 312 is provided by the host system 12 to the health care provider system 14 associated with the health care provider. The health care provider then enters refill request information in to the health care provider system 14. The refill request information is transmitted from the health care provider system 14 and received by the host system 12. The refill request information identifies a requested refill of the filled prescription, and a prescription refill authorization. For example, the health care provider can enter the following refill request information into the prescription refill screen 312: a date into the date field 318, a refill quantity in the refill quantity authorized field 320, and any message in the first message field 326. The health care provider then clicks on the send button 330 and the refill request information is delivered, through the host system 12, to the pharmacy system 16 associated with the pharmacist who originally filled the prescription.

The pharmacy system 16 then receives the refill request information, as indicated by a block 394. If the pharmacy system 16 happens to be logged onto the prescription verification system 10, an indicator is immediately output by the pharmacy system 16 to notify the pharmacist that the refill request information has arrived. If the pharmacist system 16 is not logged onto the prescription verification system 10, then during log in of the pharmacist system 16 to the host system 12, an indicator is displayed or otherwise output to the pharmacist that a message has been received in their message box. The pharmacist will then partially or completely fill the refill prescription and enter in a quantity filled of the medication into the quantity filled field 322. The pharmacist then click on the save button 332 and the process branches to the step 370 as indicated by a line 400 wherein a verification of the requested refill is generated by the host system 12 including a unique prescription identification code identifying the requested refill whereby a pharmacist associated with a pharmacy system is authorized to provide the refill of the filled prescription to the patient.

One example of the operation of the present invention provides a method for verifying prescriptions provided by a plurality of health care providers for a plurality of patients which can be filled through any one of a variety of patient-selected pharmacies with each health care provider being provided with the health care provider system 14 (see FIG. 1) and each pharmacy being provided with the pharmacy system 16 (see FIG. 1). The health care provider diagnoses a patient's condition and determines the appropriate treatment, including prescription medication.

The health care provider initiates the health care provider system at the step 102 (see FIG. 4), and connects to the host system 12 at the step 104 (see FIG. 4). The host system 12 verifies that the health care provider system 14 is a valid health care provider system 14 at step 158 (see FIG. 6). The health care provider system selects, at the step 200, the option to enter a new prescription. The health care provider then inputs via the input device 40 (see FIG. 2) prescription information associated with the medication intended to treat the patient's condition into one of the health care provider systems 14 at the step 204 (see FIG. 7).

The prescription information includes a prescribed drug intended to treat a condition associated with the patient, and a dosage level for the prescribed drug, the drug label contents and any applicable notes on the bottle, a unique health care provider code identifying the health care provider, and a patient code uniquely identifying the patient. The prescription information is then transmitted to the central processing unit 44 (see FIG. 2), via the line 48, and then communicated to the host system 12 (see FIG. 1) along the communication channel 18. The prescription information is then received by the host system 12 at the step 206 (see FIG. 7), and then the host system 12 generates a unique identification code associated with the prescription information and an initial confirmation code indicating whether the prescription has been filled, as indicated by the step 212 (see FIG. 7).

The host system 12 stores the prescription information including the unique identification code associated with the prescription information, and the initial confirmation code indicating whether the prescription contained in the prescription information has been filled at the step 214 (see FIG. 7). The health care provider can then print, via the printer 46 (see FIG. 2), a hard-copy of the prescription to give to the patient.

The patient then selects a pharmacy to fill the prescription and provides the pharmacist associated with the selected pharmacy with the prescription information, such as the hard-copy furnished by the health care provider. The pharmacist then initiates the pharmacy system 16 (see FIG. 1), indicated by the step 122 (see FIG. 5), and connects to the host system 12 at the step 124. Using the input device 70 (see FIG. 2) of the pharmacy system 16, the pharmacist then selects the fill prescription option 168 (see FIG. 7) and inputs the search information associated with the prescription, such as the unique identification code associated with the prescription provided on the printout or hard copy provided by the health care provider system 14 when the prescription was entered into the host system 12, into the host system 12, as indicated by the step 222. The search information is transmitted to the central processing unit 74 (see FIG. 3) on the pharmacy system 16 via the line 78 and then to the host system 12 via the communication channel 20.

The host system 12 receives the search information, at the step 226 (see FIG. 7), and determines whether the search information corresponds with prescription information maintained in the database on the host system 12. The host system 12 may then transmit, at a step 234, to the pharmacy system 16, prescription information including the unique health care provider code identifying the health care provider, the patient code uniquely identifying the patient, the prescription information identifying the prescribed drug and dosage level, the drug label contents and any applicable notes to be included on the bottle given to the patient and containing the prescribed drug, and the confirmation code indicating whether the prescription has been filled. Where no prescription information in the database on the host system corresponds to the search information received from the pharmacy system 16, the host system 12 transmits, at a step 238, a signal to the pharmacy system 16 indicative of the search information being invalid.

If it was determined that the search information corresponds with prescription information maintained in the database on the host system 12, the pharmacist then perceives the prescription information on the pharmacy system 16 on the output device 72 (see FIG. 3) and, for example, reviews the hard copy or printout provided to the pharmacist by the patient for alteration, and/or prints the prescription information using the printer 76. The pharmacist then fills the prescription in accordance with the prescription information when the confirmation code included in the requested prescription information indicates that the prescription has not been filled, or the pharmacist can reject the prescription when the confirmation code included in the requested prescription information indicates that the prescription has been filled.

The pharmacist, using the pharmacy system 16, then selects the option to confirm filling a prescription, as indicated by the step 170 (see FIG. 7). The pharmacist then inputs using the input device 70 (see FIG. 3) of the pharmacy system 16 a confirmation code into the host system 12 via communication channel 20 at the step 244 (see FIG. 7). The confirmation code indicates that the prescription identified by the prescription information has been filled by the patient-selected pharmacist. The host system 12 then stores the confirmation code with the prescription information associated with the prescription into the database on the host system 12. The confirmation code indicating that the prescription has been filled is available to the health care provider systems 14 and the plurality of pharmacy systems 16 so as to indicate that the prescription has been filled or rejected.

From the above description it is clear that the present invention is well adapted to carry out the objects and to attain the advantages mentioned herein as well as those inherent in the invention. While one embodiment of the invention has been described for purposes of this disclosure, it will be understood that numerous changes may be made which will readily suggest themselves to those skilled in the art and which are accomplished within the spirit of the invention disclosed herein and defined in the appended claims.

What is claimed:

1. A method for renewing prescriptions, comprising:
   submitting, by a member pharmacy via a pharmacy computer system, a login request, including a password associated with the member pharmacy, to an internet website comprising processors and non-transitory memory storing records for a plurality of patients, each of the records containing a set of prescription information including a unique health care provider code identifying a particular member health care provider who prescribed the prescription, and a patient code uniquely identifying the patient receiving the prescription, one or more of the records containing prescription information indicative of filled prescriptions, the internet website also storing pharmacy passwords for verifying the identity of a plurality of member pharmacies, and also storing health care provider passwords for verifying the identity of a plurality of member health care providers;
   verifying, with the processors using the stored pharmacy passwords, that the login request is associated with one of the member pharmacies;
   providing, from the processors via the internet website an electronic prescription renewal screen to the pharmacy computer system, the prescription renewal screen being associated with a previously filled prescription;
   receiving, by the processors via the Internet website, information indicative of a refill request from the pharmacy computer system, the refill request identifying a requested refill of the previously filled prescription;
   identifying, by the processors using the records, the member health care provider that prescribed the prescription;
   receiving, by the processors, a login request from a provider computer system associated with the member health care provider that prescribed the prescription, the login request including the password associated with the member health care provider;
   verifying, by the processors using the stored health care provider passwords, that the login request is associated with the member health care provider identified by the previously filled prescription;
   transmitting, by the processors via the internet, the refill request through the internet website to the provider computer system;
   receiving, by the processors via the internet, an authorization from the provider computer system authorizing the refill request of the previously filled prescription;
   transmitting, by the internet website via the internet, the authorization to the pharmacy computer system from which the refill request originated; and
   fulfilling, by the member pharmacy, a refill prescription for a patient based on the transmitted authorization.

2. The method of claim 1, further comprising outputting, by the internet website, a report to a computer associated with a user other than a member health care provider or a member pharmacy.

3. The method of claim 1, wherein the authorization includes a message from the member health care provider.

4. The method of claim 1, further comprising generating, by the internet website, a new database record for the refill prescription.

5. The method of claim 2, wherein the user is associated with a governmental entity.

6. The method of claim 2, wherein the user is associated with an insurance company.

7. The method of claim 2, wherein the report is summarized by a name of the member health care provider.

8. The method of claim 1, further comprising outputting, by the internet website, a patient prescription history, wherein the patient prescription history includes previous patient prescriptions associated by at least one of a patient code, a health care provider code, and a pharmacy code.

9. The method of claim 1, further comprising determining, by the internet website, whether the member health care provider identified by the previously filled prescription is logged onto the internet website prior to transmitting the refill request to the provider computer system associated with the member health care provider identified by the previously filled prescription.

10. The method of claim 9, further comprising notifying, by the internet website, the member health care provider that the refill request has been received.

11. The method of claim 10, wherein notifying the member health care provider that the refill request has been received comprises transmitting an indicator to the provider computer system associated with the member health care provider identified by the previously filled prescription.

12. The method of claim 1, further comprising delivering, by the internet website, the refill request to a message box for delivery to the member health care provider prior to transmitting the refill request to the provider computer system associated with the member health care provider.

13. A method for renewing prescriptions, comprising:
    submitting, by a member pharmacy via a pharmacy computer system, a login request, including a password associated with the member pharmacy, to an internet website comprising processors and non-transitory memory storing records for a plurality of patients, each of the records containing a set of prescription information including a unique health care provider code identifying a particular member health care provider who prescribed the prescription, and a patient code uniquely identifying the patient receiving the prescription, one or more of the records containing prescription information indicative of filled prescriptions, the internet website also storing pharmacy passwords for verifying the identity of a plurality of member pharmacies, and also storing health care provider passwords for verifying the identity of a plurality of member health care providers;
    receiving, by the member pharmacy, upon verification of the login request based on comparison of the submitted password and the stored pharmacy passwords, from the processors via the internet website, an electronic prescription renewal screen, the prescription renewal screen being associated with a previously filled prescription for a patient;
    submitting, by the pharmacy computer system to the processors via the internet website through the electronic prescription renewal screen, a refill prescription request having information identifying a requested refill of the previously filled prescription for the patient;

receiving, by the pharmacy computer system via the internet website, authorization of the refill prescription request, the authorization based on the internet website (1) identifying, using the records, the member health care provider that prescribed the prescription, (2) receiving a login request from a provider computer system associated with the member health care provider that prescribed the prescription, the login request including the password associated with the member health care provider, (3) verifying, using the stored health care provider passwords, that the login request is associated with the member health care provider identified by the previously filled prescription, and (4) receiving via the internet the authorization from the provider computer system authorizing the requested refill of the previously filled prescription; and fulfilling, by the member pharmacy, a refill prescription for the patient based on the transmitted authorization.

\* \* \* \* \*

UNITED STATES PATENT AND TRADEMARK OFFICE
CERTIFICATE OF CORRECTION

PATENT NO. : 9,501,623 B2
APPLICATION NO. : 13/572851
DATED : November 22, 2016
INVENTOR(S) : Lawrence A. Denny It is certified that error appears in the above-identified patent and that said Letters Patent is hereby corrected as shown below:

In the Claims

Column 17, Line 40: Delete "Internet" and replace with -- internet --

Signed and Sealed this
Twenty-first Day of February, 2017

Michelle K. Lee
*Director of the United States Patent and Trademark Office*